United States Patent [19]

Nagao et al.

[11] 4,416,819
[45] Nov. 22, 1983

[54] PROCESS FOR PREPARING 1,5-BENZOTHIAZEPHINE DERIVATIVES

[75] Inventors: Susumu Nagao, Takasaki; Katsuhiko Kurabayashi, Annaka; Nobuyuki Futamura, Maebashi; Hidefumi Kinoshita, Takasaki; Toshio Takahashi, Annaka, all of Japan

[73] Assignee: Tanabe Seiyaku Co., Ltd., Japan

[21] Appl. No.: 396,734

[22] Filed: Jul. 9, 1982

[51] Int. Cl.³ .................................. C07D 281/02
[52] U.S. Cl. ................................... 260/293.3 B
[58] Field of Search ........................ 260/239.3 B

[56] References Cited
FOREIGN PATENT DOCUMENTS 1805714 6/1969 Fed. Rep. of Germany ... 260/239.3 B

OTHER PUBLICATIONS

Kugita et al., "Chem. Pharm. Bull." vol. 18, No. 10, pp. 2028–2037 (1970).
Kugita et al., "Chem. Pharm. Bull." vol. 19, No. 3, pp. 595–602 (1971).

Primary Examiner—Robert T. Bond
Attorney, Agent, or Firm—Jordan B. Bierman; Linda Bierman

[57] ABSTRACT

A process for preparing 1,5-benzothiazepine derivatives of the formula:

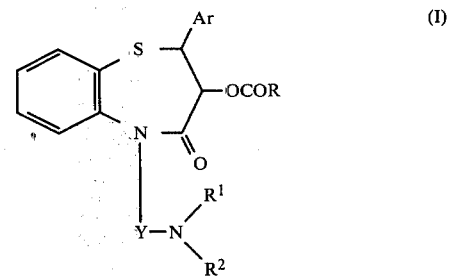

wherein Ar is a phenyl substituted with a lower alkoxy, R is a lower alkyl, $R^1$ and $R^2$ are each a lower alkyl, and Y is a lower alkylene, which have excellent coronary vasodilating and psychoneurotic activities and are useful particularly as a $Ca^{++}$-antagonistic coronary vasodilator.

11 Claims, No Drawings

PROCESS FOR PREPARING 1,5-BENZOTHIAZEPHINE DERIVATIVES

The present invention relates to a process for preparing 1,5-benzothiazepine derivatives having excellent coronary vasodilating and psychoneurotic activities. More particularly, it relates to a process for preparing 1,5-benzothiazepine derivatives of the formula:

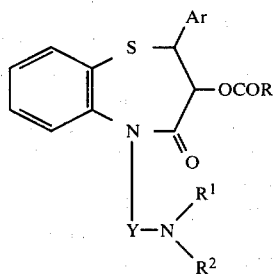

wherein Ar is a phenyl substituted with a lower alkoxy, R is a lower alkyl, $R^1$ and $R^2$ are each a lower alkyl, and Y is a lower alkylene.

In the present specification, the term "lower alkoxy" denotes an alkoxy having 1 to 4 carbon atoms (e.g. methoxy, ethoxy, n-propoxy, isopropoxy, n-butoxy, isobutoxy, sec-butoxy, tert-butoxy). The "lower alkyl" denotes an alkyl having 1 to 4 carbon atoms (e.g. methyl, ethyl, n-propyl, isopropyl, n-butyl, isobutyl, tert-butyl). The "lower alkylene" denotes an alkylene having 1 to 4 carbon atoms (e.g. methylene, ethylene, propylene, butylene).

Particularly preferred 1,5-benzothiazepine derivative prepared by the present invention is a compound of the formula (I) wherein Ar is p-methoxyphenyl, R is methyl, Y is ethylene, and $R^1$ and $R^2$ are both methyl, which has excellent coronary vasodilating activity and is particularly useful as a $Ca^{++}$-antagonistic coronary vasodilator.

According to the present invention, the compound of the formula (I) is prepared by reacting a 1,5-benzothiazepine derivative of the formula (II), preferably an alkali metal salt thereof on the nitrogen atom at 5-position, with a compound of the formula (III) as shown in the following reaction scheme-I.

Reaction scheme-I

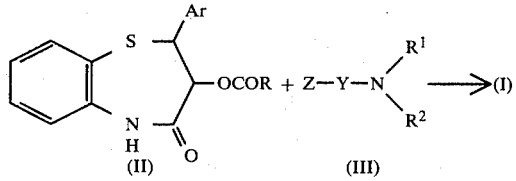

wherein Ar, R, $R^1$, $R^2$ and Y are as defined above, and Z is a halogen such as chlorine or bromine.

The condensation reaction, i.e. N-alkylation in the above reaction scheme-I can usually be carried out in an aprotic polar solvent, preferably in the presence of silica gel and/or alumina. The compound (II) is preferably reacted with the compound (III) after converted into an alkali metal salt thereof on the nitrogen atom at 5-position which is prepared by treating the compound (II) with an alkali metal hydride (e.g. sodium hydride) in an amount of 1 to 1.5 mole to 1 mole of the compound (II).

The alkali metal salt of the compound (II) may be formed in the reaction system, that is, the reaction is carried out by dissolving the compound (II) in an aprotic polar solvent, adding thereto silica gel and/or alumina, adding thereto an alkali metal hydride (whereby the compound (II) is converted into an alkali metal salt), and then reacting thereto the compound (III), wherein the compound (III) may be added to the reaction system before converting the compound (II) into an alkali metal salt thereof. In the reaction, the compound (III) is used in an amount of 1 to 3 mole to 1 mole of the compound (II). The reaction is usually carried out at a temperature of 5° to 60° C., preferably 15° to 40° C., which may vary in accordance with the kinds of the solvent and the compound (III), for about 1 to 24 hours, preferably 3 to 10 hours.

The silica gel and alumina used in the above reaction may be any commercially available products, but preferably, they are used after dehydrated by calcination (heating). The amount of the silica gel and alumina is not critical, but is usually in the range of 0.01 to 2 parts by weight to 1 part by weight of the compound (II). The particle size of the silica gel and alumina is not critical, either, and any product usable for column chromatography can be used.

The aprotic polar solvent includes, for example, dimethylsulfoxide, sulfolane, N,N-dimethylformamide, N,N-dimethylacetamide, 1,3-dimethyl-2-imidazolidinone, N-methylpyrrolidone, hexamethyl phosphortriamide, or the like, among which dimethylsulfoxide is particularly preferable.

The compound (I) thus prepared can be isolated from the reaction mixture by conventional methods, for example, by neutralizing the reaction mixture, removing the remaining reagents (e.g. silica gel, alumina, etc.) by filtration, adding a non-polar solvent to the filtrate, and after optionally washing the mixture with water and drying, crystallizing the product by evaporating the solvent. According to this process, the desired compound (I) can be obtained in a high yield (e.g. 70 to 80%) and in a high purity.

The starting 1,5-benzothiazepine derivative of the formula (II) is preferably prepared by treating a 2-hydroxy-3-(2'-aminophenylthio)-3-phenylpropionic acid of the formula (IV) with an acylating agent as shown in the following reaction scheme-II:

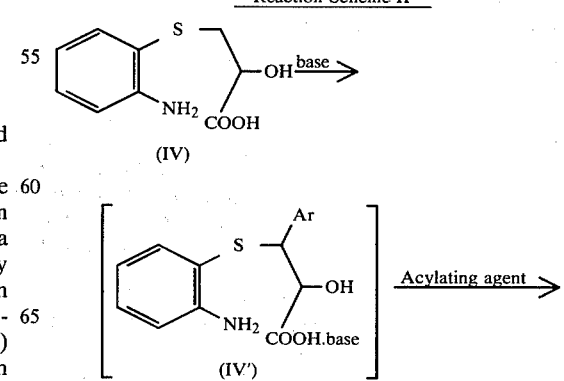

-continued
Reaction Scheme-II

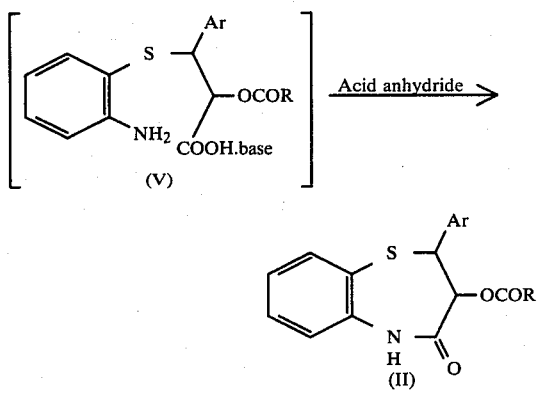

wherein Ar and R are as defined above.

The compound (IV) is firstly converted into a salt (IV') of a base such as a pyridine compound, a tertiary amine, an alkali metal or an alkiline earth metal and then reacted with an acylating agent in an appropriate solvent.

The base used therein includes, for example, pyridine compounds (e.g. pyridine, α-picoline, β-picoline, γ-picoline, a halogen-substituted pyridine, quinoline, isoquinoline), tertiary amines (e.g. trimethylamine, triethylamine), carbonates, hydrogen carbonates or organic acid salts (e.g. acetate) of alkali metal (lithium, sodium, potassium), and carbonates, hydrogen carbonates or organic acid salts (e.g. acetate) of alkaline earth metals (e.g. magnesium), among which pyridine and lithium compounds are particularly preferable. The base is usually used in an amount of 0.2 to 3 equivalents, preferably 0.5 to 2 equivalents, in case of the alkali metal or alkaline earth metal compounds, and one or more equivalents in case of the pyridine compounds and tertiary amines, to the compound (IV).

The acylating agent includes, for example, an anhydride compound of a lower alkanoic acid having 2 to 4 carbon atoms (e.g. acetic anhydride, propionic anhydride, butyric anhydride), and a halide compound of the lower alkanoic acid (e.g. acetyl chloride, acetyl bromide, propionyl chloride), which are used in an amount of equivalent or more to the compound (IV) or (IV').

The solvent is not restricted unless it gives undesirable effect on the reaction, and includes, for example, benzene, chloroform, ethyl acetate, N,N-dimethylformamide, 1,3-dimethyl-2-imidazolidinone, or the like. When the pyridine compounds or tertiary amines are used as the base, they may also be used as a solvent.

The reaction in the above reaction scheme-II proceeds different way in accordance with the kind and amount of the acylating agent. When an anhydride of a lower alkanoic acid is used in an amount of two or more equivalents, usually 2 to 2.5 equivalents, to the compound (IV) or (IV'), the desired compound (II) is directly obtained from the compound (IV'), that is, the acylation of hydroxy group at 2-position and cyclization are done in a single procedure. In this feature, the procedure is carried out by dissolving the compound (IV) in a solvent, adding thereto a base (whereby the compound (IV) is converted into a salt (IV') of the base), adding thereto an anhydride of a lower alkanoic acid in an amount of two or more equivalents, usually 2 to 2.5 equivalents, to the compound (IV) or (IV'), and then reacting the mixture at a temperature of 0° to 50° C., preferably 15° to 35° C., for a few to several hours, usually 2 to 3 hours. According to this procedure, the compound (IV') may firstly be acylated with one equivalent of the acid anhydride to form an intermediate compound of the formula (V), and the intermediate compound (V) may be cyclized in the presence of the remaining acid anhydride, but these acylation and cyclization are done approximately simultaneously within a short period of time such as 2 to 3 hours, and thereby, the desired compound (II) is obtained in a high yield such as 70% or higher.

When less than two equivalents (e.g. 1 to 1.5 equivalent) of an anhydride of a lower alkanoic acid is used as the acylating agent, the reaction is at least partly imcompleted, that is, at least a part of the intermediate compound (V) is not cyclized, and the reaction product is obtained in a mixture of the intermediate compound (V) and the compound (II). Besides, when 1 to 1.5 equivalent of a halide of a lower alkanoic acid is used as the acylating agent, only the intermediate compound (V) is obtained. The intermediate compound (V) can readily be cyclized to give the desired compound (II) by treating it with 1 to 1.5 equivalent of the acid anhydride.

Alternatively, the compound (II) may be prepared by acylating a compound of the formula (IV) with an acylating agent and then de-acylating the resulting intermediate compound (VII) with an amine as shown in the following reaction scheme-III:

Reaction Scheme-III

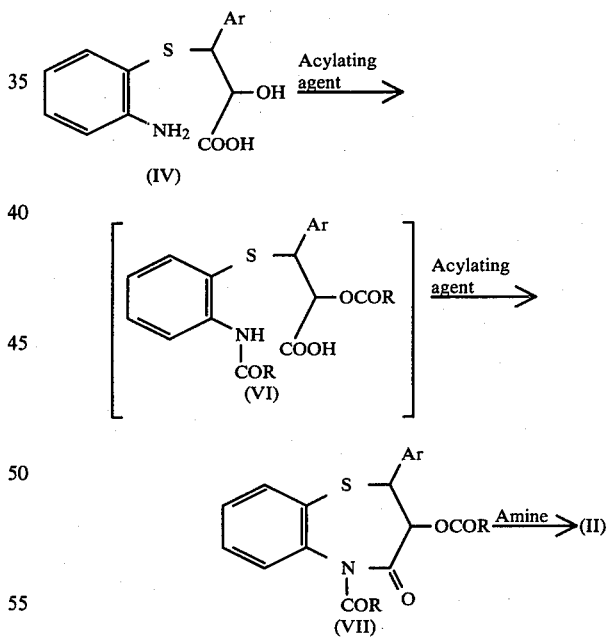

wherein Ar and R are as defined above.

The acylation of the compound (IV) is usually carried out in an appropriate solvent such as toluene, xylene, ethylbenzene by using three or more equivalents of an anhydride of a lower alkanoic acid as mentioned above at a temperature of 100° to 150° C., preferably 110° to 140° C., for a few to several hours, preferably 2 to 3 hours. When an excess amount of the acid anhydride is used, it may also be used as a solvent without using any other solvent. When less than three equivalents of the acid anhydride or two or more equivalents of a halide of a lower alkanoic acid are used as the acylaintg agent, or when the reaction is carried out at a temperature of lower than 100° C., there are produced an intermediate compound (VI) and optionally a compound wherein only amino group at 2'-position is acylated, without being cyclized. The intermediate compound (VI) can be cyclized to obtain the intermediate compound (VII) by treating it with one or more equivalents of an anhydride of a lower alkanoic acid at a temperature of 110° to 140° C., likewise.

The intermediate compound (VII) can readily be de-acylated into the compound (II) by treating it with an amine in an appropriate solvent, whereby only the acyl group on the nitrogen atom at 5-position is selectively de-acylated.

The amine used in the above de-acylation includes, for example, ammonia, hydrazine, aliphatic primary amines (e.g. methylamine, ethylamine, n-butylamine), aromatic primary amines (e.g. aniline, toluidine), aliphatic secondary amines (e.g. dimethylamine, diethylamine, di-n-propylamine, di-n-butylamine), cyclic amines (e.g. morpholine, pyrrole, imidazole), or the like, among which aliphatic secondary amines such as dimethylamine or diethylamine are preferable. These amines are used in an equimolar or excess amount to the compound (VII).

The solvent used in the de-acylation is not restricted unless it gives undesirable effect on the de-acylation reaction, and includes, for example, chloroform, benzene, toluene, xylene, N,N-dimethylformamide, or the like.

According to this de-acylation reaction, the intermediate compound (VII) can quantitatively be converted into the desired compound (II).

The compound (II) thus obtained in the above reaction scheme-II or III can be used for the condensation reaction with the compound (III) in the reaction scheme-I after being isolated or without isolation from the reaction mixture. Thus, in one preferred embodiment of the present invention, the reaction of the reaction scheme-II or III and the reaction of the reaction scheme-I are carried out continuously in the same reaction system.

The starting compounds (IV) used in the above reaction scheme-II are also known (cf. Japanese Patent Publication No. 9383/1970) or can be prepared by the same procedure as disclosed therein. That is, the compound (IV) can be prepared by reacting a 2-aminothiophenol (IX) and a glycidic acid ester of the formula (X) as shown in the following reaction scheme-IV:

Reaction Scheme-IV

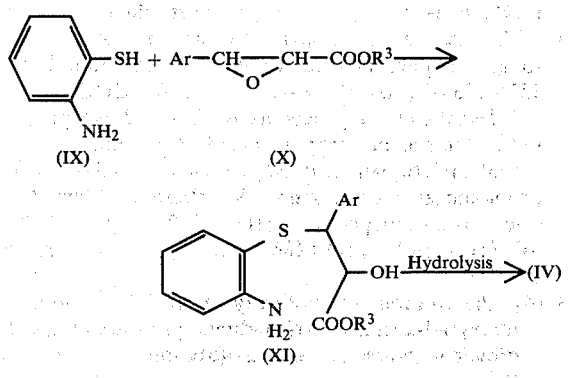

wherein Ar is as defined above, and $R^3$ is a residue of an ester.

The above reaction is usually carried out in an appropriate solvent such as toluene, xylene and ethylbenzene at a temperature of 100° to 140° C. for 5 to 20 hours, followed by hydrolyzing the resulting compound (IX) in conventional manner, for example, by treating it with an acid (e.g. hydrochloric acid, sulfuric acid) or an alkali (e.g. sodium hydroxide, potassium hydroxide).

The compound (IV) has two asymmetric carbons at 2- and 3-positions, and hence, there are two stereomers of threo isomer and erythro isomer. According to the process of the above reaction scheme-IV, the compound (IV) is obtained in the form of a threo isomer. The threo isomer includes further two optical active isomers, i.e. d-isomer and l-isomer, and it is usually obtained in a racemic mixture (dl-form). The final compound of the formula (I) has also optical activity and the d-isomer of the compound (I) is particularly useful in view of higher pharmacological activities. Although the racemic mixture of the compound (I) can be resolved into optical active isomers, the optical resolution is preferably done on the compound (IV), because the desired optical active compound (I) can be obtained from an optical active compound (IV) without racemization in the acylation and cyclization steps in the above reaction scheme-II and III and also in the N-alkylation step in the above reaction scheme-I.

The present inventors have found that the optical resolution of the compound (IV) can advantageously be done by using an optically active α-phenylethylamine as follows.

A racemic mixture of the compound (IV) is reacted with 1 to 1.2 equivalent of an optically active α-phenylethylamine, i.e. d-α-phenylethylamine or l-α-phenylethylamine, in an appropriate solvent, whereby there are obtained two diastereomer salts, which can be resolved into each optical active salt by utilizing the difference in solubility in the solvent. When d-α-phenylethylamine is used, a salt of d-isomer of the compound (IV) is isolated as a hardly soluble salt, and when l-α-phenylethylamine is used, a salt of l-isomer of the compound (IV) is isolated as a hardly soluble salt.

The solvent used in the optical resolution includes, for example, water, a hydrophilic organic solvent (e.g. methanol, ethanol, acetone), a mixture of water and a hydrophilic organic solvent, and a hydrophobic organic solvent (e.g. benzene, ethyl acetate), among which water is particularly preferable from the econimical and industrial viewpoints, because the two diastereomer salts show larger difference in solubility in water and further the hardly soluble diastereomer salt has smaller solubility in water.

The hardly soluble diastereomer salt thus obtained can be isolated from the reaction mixture by precipitating it in a conventional manner, for example, by cooling the reaction mixture, by concentrating and then cooling the reaction mixture, or by varying the component of the solvent, i.e. by adding one or more other solvents, followed by separating the precipitated salt by a conventional solid-liquid separation method, for example, by filtration, decantation, or the like. The hardly soluble diastereomer salt thus isolated has a high optical purity, usually 95% or more, and when it is recrystallized from an appropriate solvent (e.g. water, aqueous alcohol, ethyl acetate), there is obtained an optically pure diastereomer salt.

The optically active, hardly soluble diastereomer salt thus obtained can easily be converted into the corresponding free acid by a conventional hydrolysis, for example, by dissolving the hardly soluble salt in water with heating, adding thereto a mineral acid (e.g. hydrochloric acid), and separating the precipitated crystals by filtration.

Besides, as mentioned above, when d- or l-α-phenylethylamine is used, a salt of d- or l-isomer of the compound (IV) is isolated as a hardly soluble salt, respectively. Accordingly, after separating such a hardly soluble salt, other soluble isomer salt, i.e. a salt of l-isomer of the compound (IV) with d-α-phenylethylamine, or a salt of d-isomer of the compound (IV) with l-α-phenylethylamine, is contained in remaining mother liquor. The optically active compound (IV) can also be obtained from the mother liquor by adding a mineral acid (e.g. hydrochloric acid) to the mother liquor containing a soluble, optically active diastereomer salt, and separating the resulting crystals, whereby the desired optically active compound (IV) can be isolated in the form of a free acid.

The optically active α-phenylethylamine used in the above optical resolution can almost quantitatively be recovered from the solution after separating the optically active compound (IV) by filtration in a conventional manner, for example, by making alkaline the acidic filtrate obtained after separating the optically active compound (IV) with an alkali (e.g. sodium hydroxide, potassium hydroxide), extracting the solution with a hydrophobic organic solvent (e.g. benzene, ethyl acetate, ether) and removing the solvent from the extract.

The optically active compound (IV) is preferably used as the starting material in the acylation and cyclization reaction as is shown in the reaction scheme-II or III, but the starting compound (IV) may also be used in the form of an optically active diastereomer salt with an optically active α-phenylethylamine without being converted into a free acid thereof.

The present invention is illustrated by the following Examples, but it should not be construed to be limited thereto.

EXAMPLE 1

(1) Preparation of 2-hydroxy-3-(2'-aminophenylthio)-3-(4''-methoxyphenyl)propionic acid [Compound (IV) in the threo form]:

2-Aminothiophenol (14.38 g) and methyl 3-(4'-methoxyphenyl)glycidate (20.80 g) are dissolved in toluene (100 ml), and the solution is refluxed under nitrogen gas for 6 hours. The reaction mixture is concentrated, and thereto is added ethanol with heating. After cooling the mixture, the precipitated crystals are separated by filtration and recrystallized from ethanol to give methyl threo-2-hydroxy-3-(2'-aminophenylthio)-3-(4''-methoxyphenyl)propionate (27.31 g, 82%), m.p. 92°–93° C.

The product (16.65 g) is added to a 5% aqueous sodium hydroxide (80 ml), and the mixture is stirred at 50° C. for 30 minutes. After cooling to room temperature, the reaction mixture is neutralized with hydrochloric acid. The precipitated crystals are separated by filtration, washed with water and dried to give a racemic mixture of the title compound (IV) in the threo form (15.63 g, 98%), m.p. 169°–172° C.

(2) Optical resolution of the compound (IV):

The racemic mixture of the compound (IV) in the threo form (6.38 g) obtained above and d-α-phenylethylamine (2.58 g) are dissolved in water (100 ml) with heating, and the mixture is stirred at room temperature for 5 hours. The precipitated crystals are separated by filtration and recrystallized from water (60 ml) to give an optically pure salt of d-isomer of the threo compound (IV) with d-α-phenylethylamine (3.95 g), m.p. 157°–158° C., $[\alpha]_D^{23} = +376°$ (c=0.511, ethanol).

The above procedure is repeated except that the solvents as shown in Table 1 are used instead of water. The results are shown in Table 1.

TABLE 1

| Solvent | | Yield of the salt (g) | $[\alpha]_D^{23}$ (in ethanol) of the salt |
|---|---|---|---|
| Kind | Amount (ml) | | |
| Ethanol | 6 | 0.36 | +362.4° (c = 0.521) |
| 50% ethanol-H$_2$O | 10 | 0.70 | +374.0° (c = 0.475) |
| 25% ethanol-H$_2$O | 20 | 0.89 | +369.4° (c = 0.438) |
| Isopropanol | 4 | 0.89 | +333.8° (c = 0.535) |
| Benzene | 30 | 0.58 | +333.0° (c = 0.565) |
| Ethyl acetate | 2.5 | 0.59 | +337.2° (c = 0.522) |

The product obtained above is dissolved in water (180 ml) with heating, and is added thereto 1 N HCl (8.9 ml), and the mixture is cooled. The precipitated crystals are separated by filtration, washed with water and dried to give an optically pure d-isomer of the threo compound (IV) (2.68 g, 84%), m.p. 138°–139° C. $[\alpha]_D^{23} = +346°$ (c=0.355, ethanol).

To the mother liquor obtained after separating the salt of d-isomer of the compound (IV) and d-α-phenylethylamine is added 1 N HCl (8.5 ml), and the precipitated crystals are separated by filtration, washed with water and dried to give an l-isomer of the threo compound (IV) (2.40 g), $[\alpha]_D^{23} = -306°$ (c=0.360, ethanol), optical purity: 88.7% [as l-isomer of the compound (IV)].

(3) Preparation of optically active 2-(4'-methoxyphenyl)-3-acetoxy-2,3-dihydro-1,5-benzothiazepin-4(5H)-one [Compound (II)]:

Threo-d-2-hydroxy-3-(2'-aminophenylthio)-3-(4''-methoxyphenyl)propionic acid [Compound (IV)] (3.19g) is dissolved in N,N-dimethylformamide (5 ml), and thereto is added pyridine (0.80 ml). The mixture is stirred at room temperature for 30 minutes. After acetic anhydride (2.04 g) is added dropwise to the mixture, the reaction mixture is continuously stirred for one hour. The resulting reaction mixture is added to ice-water (200 ml), and the precipitated crystals are separated by filtration, washed with water and dried to give a d-cis-compound (II) (2.80 g, 81.6%), m.p. 150°–152° C. This products is subjected to thin layer chromatography with silica gel (developer, benzene:ethyl acetate=4:1) to give a pure product of the title compound, m.p. 152°–153° C., $[\alpha]_D^{21.5} = +39°$ (c=0.500, CHCl$_3$).

When the above procedure is repeated except that a salt of the starting propionic acid compound (IV) with d-α-phenylethylamine (0.50 g) is used instead of the free propionic acid compound (IV), there is obtained the title d-cis-compound (II) (0.27 g, 69.3%), $[\alpha]_D^{23} = +38.1°$ (c=0.486, CHCl$_3$) (optical purity: 97.7%).

(4) Preparation of optically active 2-(4'-methoxyphenyl)-3-acetoxy-5-(N,N-dimethylaminoethyl)-2,3-dihydro-1,5-benzothiazepin-4(5H)-one [Compound (I)]:

The d-cis-compound (II) obtained above (1.0 g) and dried silica gel (Wako-gel C-200) suitable for column chromatography (0.50 g) are added to dried dimethylsulfoxide (10 ml), and thereto is added a 60% by weight sodium hydride (0.14 g), and the mixture is stirred at room temperature for 30 minutes. To the reaction mixture is added a 50% by weight solution (0.75 g) of N,N-dimethylaminoethyl chloride in ether. After stirring at room temperature for 5 hours, the reaction mixture is neutralized with acetic acid, and then silica gel is filtered off. To the filtrate is added benzene, and the benzene solution is washed with water and dried. Benzene is distilled off from the solution to give an oily substance (1.27 g).

The oily substance thus obtained is dissolved in ether, and thereto is added ether saturated with hydrochloric acid. The resulting crystals are separated by filtration and recrystallized from ethanol-isopropanol to give a d-cis-form hydrochloride product of the title compound (I) (1.01 g, 76.9%), m.p. 206°–207° C., $[\alpha]_D^{27} = +96.6°$ (c=0.613, methanol).

EXAMPLE 2

Preparation of 2-acetoxy-3-(2'-aminophenylthio)-3-(4''-methoxyphenyl)propionic acid [free acid of Compound (V)]:

2-(1). 2-Hydroxy-3-(2'-aminophenylthio)-3-(4''-methoxyphenyl)propionic acid [Compound (IV)] (3.19 g) is dissolved in pyridine (10 ml), and thereto is added dropwise acetic anhydride (1.02 g) at 10° C., and the mixture is stirred at the same temperature for 2 hours. The reaction mixture is added to ice-water (200 ml), neutralized with hydrochloric acid and is extracted with benzene (50 ml×2). The benzene extracts are combined, washed with water and dried, and then evaporated to remove benzene to give free acid of the compound (V) (3.07 g, 85.0%), m.p. 104°–107° C.

2-(2). In the same manner as described in the above Example 2-(1) except that acetyl chloride (0.79 g) is used instead of acetic anhydride and further the reaction mixture is extracted with chloroform (50 ml) instead of benzene, the reaction is carried out to give free acid of the compound (V) (3.14 g, 87%).

2-(3). In the same manner as described in the above Example 2-(1) except that triethylamine (1.50 g) is used instead of pyridine, the reaction is carried out to give free acid of the compound (V) (2.89 g, 80%).

EXAMPLE 3

Preparation of 2-(4'-methoxyphenyl)-3-acetoxy-2,3-dihydro-1,5-benzothiazepin-4(5H)-one [Compound (II)]:

3-(1). 2-Acetoxy-3-(2'-aminophenylthio)-3-(4''-methoxyphenyl)propionic acid [free acid of Compound (V)] (3.00 g) is dissolved in pyridine (6 ml), and the mixture is stirred at room temperature for 30 minutes. After adding dropwise acetic anhydride (0.85 g), the mixture is further stirred at room temperature for 30 minutes. The reaction mixture is added to ice-water (100 ml), and the precipitated crystals are separated by filtration, washed with water and dried to give the title compound (II) (2.42 g, 84.9%), m.p. 198°–200° C.

3-(2). 2-Hydroxy-3-(2'-aminophenylthio)-3-(4''-methoxyphenyl)propionic acid [Compound (IV)] (0.5 g) is dissolved in pyridine (2 ml), and the mixture is stirred at room temperature for one hour. After adding dropwise acetic anhydride (0.32 g) over a period of 30 minutes, the mixture is further stirred at room temperature for 1.5 hour. The reaction mixture is treated in the same manner as described in the above 3-(1) to give the title compound (II) (0.48 g, 89%), m.p. 198°–200° C. When this product is recrystallized from ethanol, there is obtained a pure product thereof, m.p. 200°–202° C.

3-(3). The same compound (IV) as used in the above 3-(2) (1.00 g) is dissolved in N,N-dimethylformamide (2 ml), and thereto is added triethylamine (0.32 g), and the mixture is stirred at room temperature for 30 minutes. After adding acetic anhydride (0.64 g), the mixture is further stirred at room temperature for 2 hours. The reaction mixture is treated in the same manner as described in the above 3-(1) to give the title compound (II) (0.75 g, 69.8%), m.p. 193°–195° C.

3-(4). The procedure in the above 3-(3) is repeated except that 1,3-dimethyl-2-imidazolidinone is used as a solvent instead of N,N-dimethylformamide and further pyridine (0.26 g) is used instead of triethylamine to give the title compound (II) (0.90 g, 83.7%), m.p. 198°–200° C.

3-(5). The same compound (IV) as used in the above 3-(2) (3.19 g) is dissolved in N,N-dimethylformamide (25 ml), and thereto is added lithium carbonate (0.37 g), and the mixture is stirred at room temperature for one hour. After adding dropwise a solution of acetic anhydride (2.20 g) in N,N-dimethylformamide (5 ml), the mixture is further stirred at room temperature for 2 hours. The reaction mixture is added to ice-water (800 ml), and the precipitated crystals are separated by filtration, washed with water and dried to give the title compound (II) (2.81 g, 81.9%), m.p. 196°–198° C.

3-(6). The procedure in the above 3-(5) is repeated except that a 50% by weight sodium hydride (0.53 g) is used instead of lithium carbonate to give the title compound (II) (2.13 g, 62.1%), m.p. 192°–196° C.

3-(7). The same compound (IV) as used in the above 3-(2) (0.50 g) is dissolved in α-picoline (2 ml), and the mixture is stirred at room temperature for 30 minutes. After adding dropwise acetic anhydride (0.32 g) over a period of one hour, the mixture is further stirred at room temperature for one hour. The reaction mixture is treated in the same manner as described in the above 3-(1) to give the title compound (II) (0.38 g, 70.7%), m.p. 198°–200° C.

3-(8). The same compound (IV) as used in the above 3-(2) (0.30 g) is dissolved in quinoline (1 ml), and the mixture is stirred at room temperature for 30 minutes. After adding dropwise acetic anhydride (0.192 g) over a period of 30 minutes, the mixture is further stirred at room temperature for 2 hours. The reaction mixture is added to an ice-water (100 ml) and is neutralized with hydrochloric acid. The precipitated crystals are separated by filtration, washed with water and dried to give the title compound (II) (0.24 g, 74.4%), m.p. 198°–200° C.

3-(9). The procedure in the above 3-(5) is repeated except that various metallic salts as shown in Table 2 are used instead of lithium carbonate. The results are shown in Table 2.

TABLE 2

| Metallic salt | | Yield of the |
|---|---|---|
| Kind | Amount (g) | compound (II) |
| Basic magnesium carbonate | 2.91 | 2.23 g (65.0%) |
| Sodium bicarbonate | 2.52 | 2.40 g (70.0%) |
| Lithium acetate | 1.30 | 2.50 g (72.9%) |

EXAMPLE 4

Preparation of 2-(4'-methoxyphenyl)-3-propionyloxy-2,3-dihydro-1,5-benzothiazepin-4(5H)-one [Propionated Compound (II)]:

4-(1). 2-Hydroxy-3-(2'-aminophenylthio)-3-(4''-methoxyphenyl)propionic acid [Compound (IV)] (3.19 g) and pyridine (0.79 g) are dissolved in N,N-dimethylformamide (5 ml), and the solution is stirred at room temperature for 30 minutes. After adding dropwise propionic anhydride (2.60 g), the mixture is further stirred at room temperature for 1.5 hour. The reaction mixture is added to ice-water (200 ml), and the precipitated crystals are separated by filtration, washed with water and dried to give the title propionated compound (II) (3.19 g, 89.4%), m.p. 155°–156° C.

4-(2). The same compound (IV) as used in the above 4-(1) (3.19 g) is dissolved in 1,3-dimethyl-2-imidazolidinone (30 ml), and thereto is added lithium carbonate (0.74 g), and the mixture is stirred at room temperature for one hour. After adding dropwise propionic anhydride (2.86 g), the mixture is further stirred at room temperature for 2 hours. The reaction mixture is added to ice-water (800 ml), and the precipitated crystals are separated by filtration, washed with water and dried to give the title propionated compound (II) (3.29 g, 92.2%), m.p. 155°–156° C.

EXAMPLE 5

Preparation of 2-(4'-methoxyphenyl)-3-(acetoxy-5-(N,N-dimethylaminoethyl)-2,3-dihydro-1,5-benzothiazepin-4(5H)-one [Compound (I)]:

5-(1). 2-(4'-Methoxyphenyl)-3-acetoxy-2,3-dihydro-1,5-benzothiazepin-4(5H)-one [Compound (II)] (1.0 g) and dried silica gel suitable for column chromatography (which is obtained by calcining a commercially available silica gel (Wako gel C-200) at 300° C. under nitrogen for 8 hours) (0.5 g) are added to dimethylsulfoxide (10 ml), and thereto is added a 60% by weight sodium hydride (0.14 g), and the mixture is stirred at room temperature for 30 minutes. A 50% by weight solution (0.75 g) of N,N-dimethylaminoethyl chloride in ether is added to the mixture, and the mixture is further stirred at room temperature for 5 hours and neutralized with acetic acid, and then, silica gel is filtered off. To the filtrate is added benzene, and the benzene solution is washed with water, dried, and evaporated to remove benzene to give a solid substance (1.20 g). The solid substance is added to diisopropyl ether. After removing the insoluble materials by filtration, the filtrate is allowed to stand at room temperature. The precipitated crystals are separated by filtration to give the title compound (I) (0.92 g, 76.2%), m.p. 134°–135° C. The hydrochloride of this product: m.p. 187°–188° C.

The above procedure is repeated except that a commercially available silica gel is used as it stands instead of the dried silica gel and sodium hydride is used in an amount of 0.16 g. As a result, there is obtained the title compound (I) in a yield of 67.9%.

5-(2). The procedure of the above 5-(1) is repeated except that a dried alumina suitable for column chromatography (which is obtained by calcining a commercially available alumina at 300° C. under nitrogen for 8 hours) (200 mesh, 0.5 g) is used instead of silica gel to give the title compound (I) (0.87 g, 72.1%).

The above procedure is repeated except that a commercially available alumina is used as it stands of the dried alumina and sodium hydride is used in an amount 0.18 g. As a result, there is obtained the title compound (I) in a yield of 57.1%.

5-(3). The procedure of the above 5-(1) is repeated except that various aprotic polar solvents shown in Table 3 are used instead of dimethylsulfoxide and the reaction period of time is 20 hours. As a result, the title compound (I) is obtained in a yield as shown in Table 3.

TABLE 3

| Aprotic polar solvents | Silica gel or alumina | Yield of the compound (I) |
| --- | --- | --- |
| N,N—Dimethylformamide | Dried silica gel | 70% |
| N,N—Dimethylformamide | Dried alumina | 65% |
| N—Methylpyrrolidone | Dried silica gel | 72% |
| N,N'—Dimethylimidazolidinone | Dried silica gel | 63% |
| Hexamethylphosphoryltriamide | Dried silica | 71% |
| N,N'—Dimethylacetamide | Dried silica gel | 68% |
| Sulfolane | Dried silica gel | 71% |

EXAMPLE 6

Preparation of 2-(4'-methoxyphenyl)-3-acetoxy-5-acetyl-2,3-dihydro-1,5-benzothiazepin-4(5H)-one [Compound (VII)]:

6-(1). 2-Hydroxy-3-(2'-aminophenylthio)-3-(4''-methoxyphenyl)propionic acid [Compound (IV)] (3.19 g) and acetic anhydride (6.12 g) are added to xylene (10 ml), and the mixture is refluxed for 2 hours while the produced acetic acid is removed by azeotropic distillation. After the reaction is finished the reaction mixture is cooled to room temperature, and the precipitated crystals are separated by filtration, washed and dried to give the title compound (VII) (3.28 g, 85.2%), m.p. 158°–160° C. When this product is recrystallized from xylene, there is obtained the pure product, m.p. 160°–161° C.

6-(2). The same compound (IV) as used in the above 6-(1) (3.19 g) and acetic anhydride (1.22 g) are added to xylene (10 ml), and the mixture is stirred at 50° C. for one hour. After the reaction, the precipitated crystals are separated by filtration, washed and dried to give 2-hydroxy-3-(2'-N-acetyl-aminophenylthio)-3-(4''-methoxyphenyl)propionic acid (3.43 g, 95.0%), m.p. 170°–171° C.

This product (3.0 g) and acetic anhydride (3.39 g) are added to xylene (10 ml), and the mixture is reacted in the same manner as described in the above 6-(1) to give the title compound (VII) (2.7 g, 84.5%), m.p. 158°–160° C.

6-(3). An N-acetyl derivative of the compound (IV) (7.22 g) and acetic anhydride (2.44 g) are added to toluene (20 ml), and the mixture is reacted at 80° C. for one hour. After cooling the reaction mixture, the precipitated crystals are separated by filtration, washed and dried to give 2-acetoxy-3-(2'-N-acetylaminophenylthio)-3-(4''-methoxyphenyl)propionic acid [Compound (VI)] (7.40 g, 91.8%), m.p. 164°–166° C.

This product (3.70 g) and acetic anhydride (1.87 g) are added to xylene (10 ml), and the mixture is reacted in the same manner as described in the above 6-(1) to give the title compound (VII) (3.0 g, 84.9%), m.p. 158°–160° C.

EXAMPLE 7

Preparation of 2-(4'-methoxyphenyl)-3-acetoxy-2,3-dihydro-1,5-benzothiazepin-4(5H)-one [Compound (II)]:

7-(1). 2-(4'-Methoxyphenyl)-3-acetoxy-5-acetyl-2,3-dihydro-1,5-benzothiazepin-4(5H)-one [Compound (VII)] (1.93 g) and diethylamine (0.44 g) are added to chloroform (20 ml), and the mixture is stirred at room temperature for one hour. After distilling off chloroform, water is added to the residue, and the precipitated crystals are separated by filtration, washed with water and dried to give the title compound (II) (1.63 g, 94.8%), m.p. 198°–200° C.

7-(2). In the same manner as described in the above 7-(1) except that dimethylamine (0.27 g) is used instead of diethylamine and further benzene (90 ml) is used instead of chloroform, the reaction is carried out to give the title compound (II) (1.54 g, 89.6%), m.p. 196°–199° C.

7-(3). The compound (VII) (200 mg) and aniline (63 mg) are added to chloroform (10 ml), and the mixture is stirred at room temperature for 2 hours. The chloroform solution is concentrated and subjected to thin layer chromatography using silica gel (developer, benzene:ethyl acetate=1:1) to give acetanilide (62 mg, 88.3%) and the title compound (II) (159 mg, 89.2%), m.p. 196°–198° C.

7-(4). The procedure of the above 7-(1) is repeated except that various amines as shown in Table 4 are used instead of dimethylamine. As a results, there is obtained the title compound (II) in the yield as shown in Table 4.

TABLE 4

| Amine | | |
|---|---|---|
| Kind | Amount (g) | Yield of the compound (II) |
| Ammonia* | 0.15 | 1.20 g (69.8%) |
| Phenylhydrazine | 0.65 | 1.35 g (78.6%) |
| n-Butylamine | 0.50 | 1.40 g (81.4%) |
| Imidazole | 0.40 | 1.50 g (87.3%) |
| Morpholine | 0.55 | 1.42 g (82.6%) |

*It is prepared by blowing ammonia gas into chloroform.

What is claimed is:

1. A process for preparing 1,5-benzothiazepine derivatives of the formula:

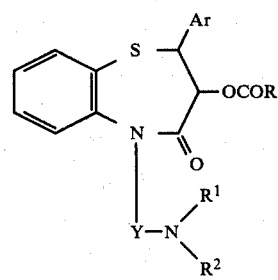

wherein Ar is a phenyl substituted with a lower alkoxy, R is a lower alkyl, $R^1$ and $R^2$ are each a lower alkyl, and Y is a lower alkylene, which comprises reacting a 2-hydroxy-3-(2'-aminophenylthio)-3-phenylpropionic acid of the formula:

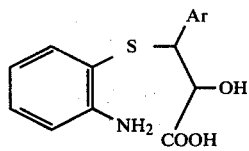

wherein Ar is as defined above which is in the form of a salt with a base, with an acylating agent, and reacting the resulting 1,5-benzothiazepine derivative of the formula:

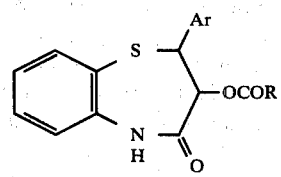

wherein Ar and R are as defined above, or an alkali metal salt thereof with a compound of the formula:

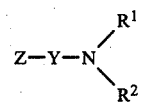

wherein $R^1$, $R^2$ and Y are as defined above, and Z is a halogen.

2. A process according to claim 1, wherein the reaction between the compound (II) and the compound (III) is carried out in the presence of silica gel and/or alumina.

3. A process according to claim 1, wherein the base to form a salt with the compound (IV) is a member selected from the group consisting of a pyridine compound, a tertiary amine, an alkali metal and an alkaline earth metal.

4. A process according to claim 1, wherein the acylating agent is an anhydride of a lower alkanoic acid which is used in an amount of two or more equivalents of the compound (IV).

5. A process according to claim 1, wherein the reaction in the first step is carried out by reacting the compound (IV) with less than two equivalents of an anhydride of a lower alkanoic acid or with one or more equivalents of a halide of a lower alkanoic acid, and reacting the resulting intermediate compound of the formula:

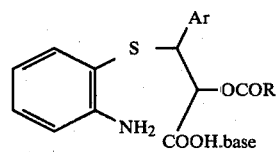

wherein Ar and R are as defined herein, with one or more equivalent of an anhydride of a lower alkanoic acid.

6. A process according to claim 1, wherein the starting 2-hydroxy-3-(2'-aminophenylthio)-3-phenylpropionic acid (IV) is used in the form of a free acid and is reacted with three or more equivalents of an acylating agent, and treating the resulting compound of the formula:

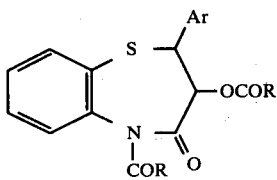

(VII)

wherein Ar and R are as defined herein, with an amine to form the compound (II).

7. A process according to claim 6, wherein the acylating agent is anhydride or halide of a lower alkanoic acid.

8. A process according to claim 6, wherein the amine is a member selected from the group consisting of ammonia, hydrazine, an aliphatic primary amine, an aromatic primary amine, an aliphatic secondary amine, and a cyclic amine.

9. A process according to any one of claim 1, 2, 3, 4, 5, 6, 7, or 8, wherein the starting compound (IV) is an optically active compound in the threo form.

10. A process according to claim 9, wherein the starting compound (IV) is a threo-d-type compound.

11. A process according to claim 9 or 10, wherein the optical active compound (IV) is prepared by subjecting a racemic mixture of the compound (IV) in the threo form to optical resolution by treating the racemic mixture of the compound (IV) with an optically active α-phenylethylamine, separating an optically active salt of the compound (IV) with an optically active α-phenylethylamine, and optionally treating the resulting optically active salt with a mineral acid to convert it to a free optically active compound (IV).

* * * * *